United States Patent [19]
Kiefer

[11] Patent Number: 5,574,223
[45] Date of Patent: Nov. 12, 1996

[54] SCAN ASSEMBLY AND METHOD USING SCAN RATE MODULATION

[75] Inventor: Karl F. Kiefer, Woodlands, Tex.

[73] Assignee: Gas Research Institute, Chicago, Ill.

[21] Appl. No.: 497,032

[22] Filed: Jun. 30, 1995

Related U.S. Application Data

[63] Continuation-in-part of Ser. No. 222,621, Apr. 5, 1994.

[51] Int. Cl.⁶ .......................... G01N 29/10; G01N 29/26
[52] U.S. Cl. ..................... 73/623; 324/220; 324/226
[58] Field of Search .......................... 73/622, 623, 638, 73/597, 634, 637, 639, 866.5, 628; 324/220, 226

[56] References Cited

U.S. PATENT DOCUMENTS

| | | | |
|---|---|---|---|
| 2,723,357 | 11/1955 | Valkenburg et al. | 310/8.7 |
| 3,714,816 | 2/1973 | Miller | 73/71.5 |
| 3,763,694 | 10/1973 | Rathburn et al. | 73/71.5 |
| 3,786,684 | 1/1974 | Wiers et al. | 73/623 |
| 4,037,465 | 7/1977 | Cook et al. | 73/623 |
| 4,055,990 | 11/1977 | Topping | 73/623 |
| 4,131,018 | 12/1978 | Muller et al. | 73/432 |
| 4,285,243 | 8/1981 | Collingwood | 73/623 |
| 4,289,025 | 9/1981 | Norel et al. | 73/152 |
| 4,302,976 | 12/1981 | Bull | 73/639 |
| 4,304,134 | 12/1981 | Rouse et al. | 73/634 |
| 4,353,257 | 10/1982 | Viba | 73/623 |
| 4,506,549 | 3/1985 | Thome | 73/582 |
| 4,581,938 | 4/1986 | Wentzell | 73/623 |
| 4,615,218 | 10/1986 | Pagano | 73/639 |
| 4,621,532 | 11/1986 | Takagi et al. | 73/623 |
| 4,691,572 | 9/1987 | van den Berg et al. | 73/643 |
| 4,718,277 | 1/1988 | Glascock | 73/622 |
| 4,735,087 | 4/1988 | Homrani et al. | 73/597 |
| 4,769,598 | 9/1988 | Krieg et al. | 324/219 |
| 4,891,972 | 1/1990 | Kawaguchi et al. | 73/623 |
| 5,007,291 | 4/1991 | Walters et al. | 73/640 |
| 5,014,711 | 5/1991 | Nagasaki | 128/660.07 |
| 5,046,033 | 9/1991 | Andreasen et al. | 364/580 |
| 5,133,220 | 7/1992 | Alford et al. | 73/866.5 |
| 5,170,346 | 12/1992 | Crawford et al. | 364/413.16 |
| 5,204,622 | 4/1993 | McCaslin et al. | 324/220 |
| 5,254,944 | 10/1993 | Holmes et al. | 324/220 |

Primary Examiner—Hezron E. Williams
Assistant Examiner—Rose M. Finley
Attorney, Agent, or Firm—Hopkins & Thomas

[57] ABSTRACT

An ultrasonic scan assembly is adapted to efficiently scan a surface and cross-section of a wall of an elongated cylindrical object. The ultrasonic scan assembly has a rotatable sensor section capable of rotating as the scan assembly is advanced axially along the elongated cylindrical object. In operation, the scan assembly is advanced in an axial direction along elongated cylindrical object, and the sensor section of the scan assembly is rotated so as to create a helical scan pattern. For at least a portion of the cylindrical object, the angular velocity of the sensor section is modulated. As a result, that portion of the cylindrical object is scanned at more than one scan rate.

9 Claims, 9 Drawing Sheets

SCAN ASSEMBLY AND METHOD USING SCAN RATE MODULATION

The present patent application is a Continuation-In-Part application of a co-pending patent application entitled "Scan Assembly Structure", filed on Apr. 5, 1994, and assigned Ser. No. 08/222,621. The foregoing application is incorporated herein by reference.

FIELD OF THE INVENTION

The present invention relates generally to the inspection of buried natural gas pipes, and more particularly, to a method of scan rate modulation for ultrasonic inspection of gas pipes by a downhole scan assembly which improves reliability and accuracy of the scan.

BACKGROUND OF THE INVENTION

Thousands of miles of buried natural gas pipes of varying size and formed from various materials are presently in service. All of these pipes are in some state of progressive degradation. In most instances, the extent of such degradation is unknown, and hence, the serviceability of the pipes is similarly unknown. This lack of information with the respect to the degree of degradation results in unforeseen gas pipe leaks and/or breaks, and necessitates the expending of substantial time and expense in locating these defects so that repairs and/or replacement can be made. Because of the need to detect conditions which might result in gas pipe breaks and/or leaks, an apparatus has been developed for inspecting gas pipes, and such apparatus is usually referred to as a pipe line "pig." Such pipe line "pigs" typically include a housing with a plurality of sensors, such as ultrasonic transducers, mounted to the outer surface thereof in a predetermined configuration or array to contact the inner surface of the gas pipe. Since the sensors are in a predetermined configuration or army, complete inspection of the wall of the gas pipe is generally not possible, i.e., the portion of the wall between two adjacent sensors is typically not inspected. Thus, to approach complete inspection of the wall would require an inordinate number of sensors. In an attempt to achieve close to complete inspection, several "pigs" have incorporated rotational movement of the sensors as the pigs advance axially down the pipe, thus producing a helical scan pattern. By increasing the rotational speed of the sensors, the helical pattern compresses, essentially increasing the percentage of the pipe inspected. A more thorough discussion of these principles is found in U.S. patent application Ser. No. 08/222,621, filed on Apr. 5, 1994, and entitled "Scan Assembly Structure", the disclosure of which is incorporated herein by reference.

However, because the pipe walls contain imperfections and are often littered with debris, ultrasonic energy introduced into a pipe wall from a transducer, at an angle perpendicular to the inside surface of the pipe at the point of entry, is not received back at the point of entry, but is reflected and refracted off the debris and/or the imperfections of the pipe at oblique or random angles. Thus, the transmitted energy is sufficiently scattered such that no response signal is detected. The absence of scan data at a particular place within a scan due to this phenomenon is referred to in the art as a "drop-out." Because of the nature of "drop-outs", merely increasing the mean rotational speed of the sensors during the scan of a discrete section of pipe does not improve the results. The debris and/or imperfection which cause a "drop-out" at one scan rate produce a similar "drop-out" at a different scan rate. Further, it is wholly impractical to make multiple scan passes of a discrete section of pipe in order to synthesize the data into a single tomographic representation of the pipe because of the extreme exactitude required to scan the exact same section multiple times. In other words, the sensors would have to be positioned in precisely the same starting position for both scan passes or the data would not correlate.

In view of the foregoing, it would be desirable to develop a method for more completely inspecting the walls of gas pipes under operating flow conditions whereby the phenomenon of "drop-outs" is minimized or eliminated. With this capability, natural gas utilities can monitor the rate of degradation of gas pipes and plan repairs and/or replacements before failures occur.

SUMMARY OF THE INVENTION

An object of the present invention is to overcome the deficiencies and inadequacies in the prior art as described above and as generally known in the industry.

Another object of the present invention is to enable more accurate and complete inspection of gas pipes under operating flow conditions.

Another object of the present invention is to improve the ability of a downhole ultrasonic scan assembly to collect data from the portions of a gas pipe having imperfections or flaws.

Another object of the present invention is to improve the signal-to-noise ratio of a downhole ultrasonic scan assembly.

Briefly stated, the present invention is an ultrasonic scan assembly and method for scanning a surface and cross-section of a wall of an elongated cylindrical object. The ultrasonic scan assembly has a rotatable sensor section capable of rotating as the scan assembly is advanced axially along the elongated cylindrical object. The scan assembly is advanced in an axial direction along the elongated cylindrical object. As the scan assembly advances, the sensor section of the scan assembly is rotated so as to create a helical scan pattern. For at least a portion of the cylindrical object, the rotational speed of the sensor section is modulated whereby that portion of the cylindrical object is scanned at more than one scan rate.

A portion of the cylindrical object is essentially scanned more than once by rotating the sensor section one full revolution of 360 degrees at a first rotational speed and then either increasing or decreasing the rotational speed of the sensor section for a second revolution. The data collected from the two scans is from substantially the same portion of the cylindrical object since the axial displacement of the scan assembly during the two revolutions of the sensor section is diminutive. The scan rate can be modulated for the complete scan of an elongated cylindrical object or merely over portions of the object experiencing "drop-outs" or portions that are known to have debris or imperfections. In addition, scan rate modulation can be incorporated with push rodded or robotic "pigs."

Other objects, features, and advantages of the present invention will become apparent from the following description when considered in conjunction with the accompanying drawings. All such additional objects, features, and advantages are intended to be included herein.

BRIEF DESCRIPTION OF THE DRAWINGS

The present invention, as defined in the claims, can be better understood with reference to the following drawings.

The drawings are not necessarily to scale, emphasis instead being placed upon clearly illustrating the principles of the invention. Moreover, like reference numerals designate corresponding parts throughout the several views.

DETAILED DESCRIPTION OF THE PREFERRED EMBODIMENT

Figure 1:
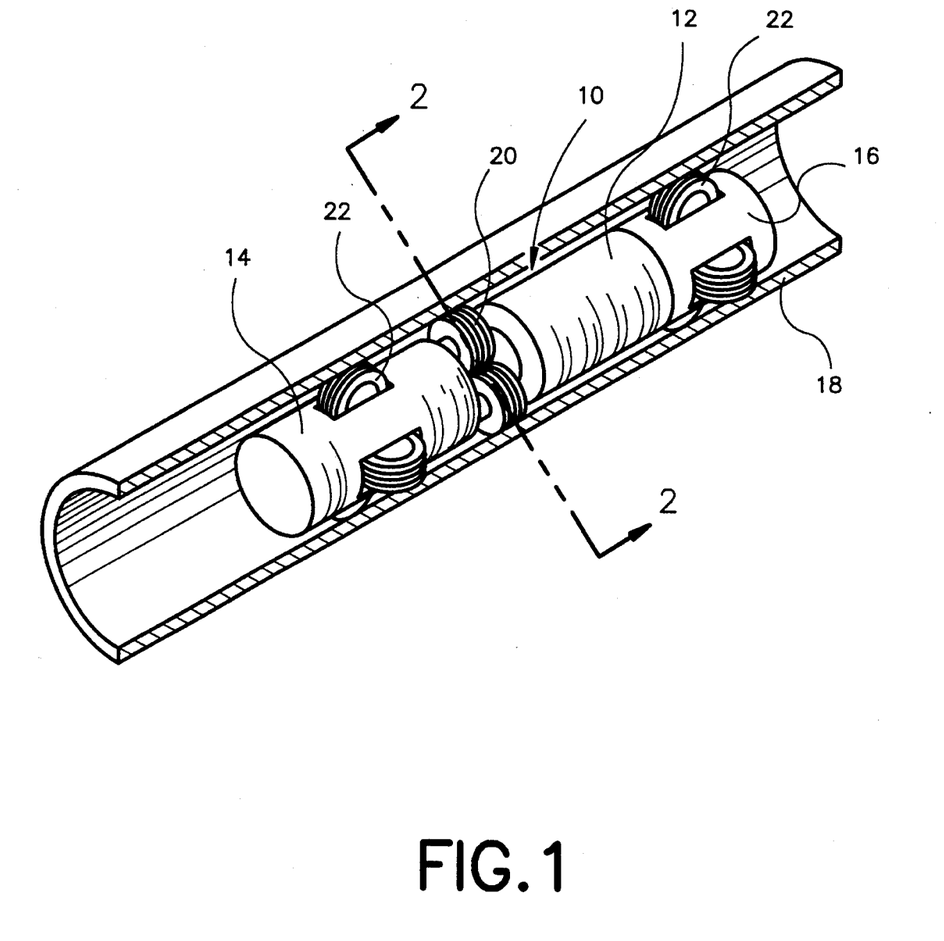
FIG. 1 is a perspective view, partially cut-away in cross-section, of a first embodiment of the scan assembly in accordance with the present invention.

Referring now to the drawings where the illustrations are for the purpose of describing the preferred embodiment of the present invention and are not intended to limit the invention described herein, FIG. 1 is a perspective view of a scan assembly 10 that can be utilized to transmit ultrasonic interrogating pulses into an object whose material is to be inspected and to receive return pulses from imperfections, flaws, or occlusions within the material or from surfaces thereon. The scan assembly 10 includes a sensor section 12 interposed between a front section 14 at one end of the scan assembly 10 and a rear section 16 at the other end thereof. The scan assembly 10 is receivable within the object to be inspected, such a gas pipe 18, and is moveable along the longitudinal axis of the gas pipe 18. The sensor section 12 includes a pair scan rollers 20 which are angularly positioned approximately 180 degrees relative to one another and canted slightly in the direction of travel of the scan assembly 10 through the gas pipe 18 so as to drive the scan assembly 10 therethrough. The canting or offsetting of the scan rollers 20 causes the scan assembly 10 to "pull" itself through the gas pipe 18 as the scan rollers 20 rotate. The front section 14 and the rear section 16 of the scan assembly 10 are provided with wheels 22 which are angularly positioned approximately 90 degrees relative to one another in each section 14, 16, and are oriented along the longitudinal axis of the assembly 10. The wheels 22 are coupled to rotation position sensors (not shown) so that movement of the scan assembly 10 within the gas pipe 18 and the location of the scan assembly 10 therein can be accurately monitored. Biasing means (not shown); e.g., a spring is provided and applies a radial outwardly directed force to each of the wheels 22, permitting the scan assembly 10 to be used within gas pipes 18 of various inner diameters.

Figure 2:
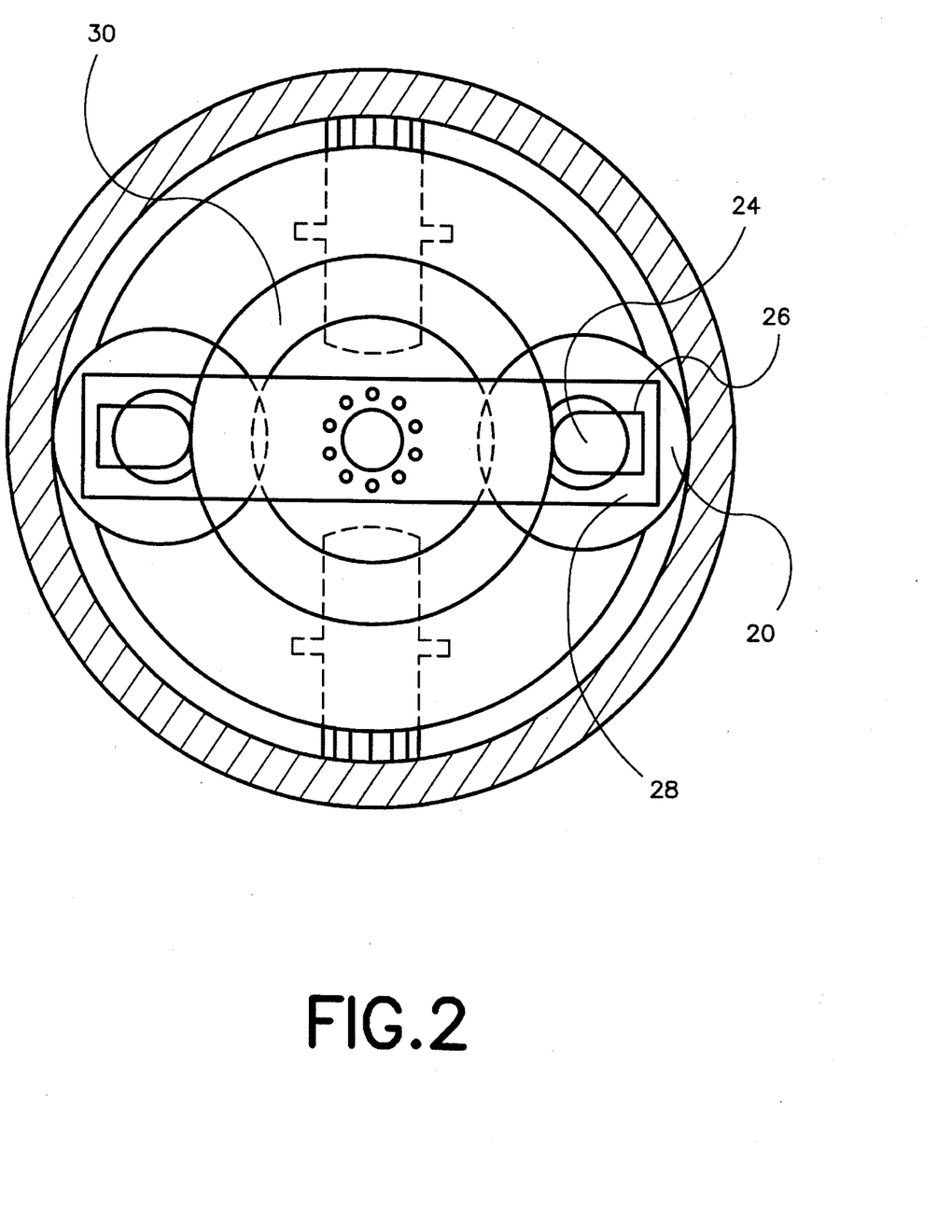
FIG. 2 is a partial cross-sectional view of the scan assembly of FIG. 1 taken substantially along lines 2—2 in FIG. 1.

Referring now to FIG. 2, an axle 24 about which a scan roller 20 rotates is received within an elongated slot 26 provided in either end of a crank arm 28 which is rotated by a scan motor 30 located within front section 14 of scan assembly 10. The elongated slot 26 permits radial movement of the scan roller 20 therein. A biasing mechanism (not shown); e.g., a spring is provided and applies a radial outwardly directed force to the axle 24 and the scan roller 20 causing the scan roller 20 to grippingly engage the surface defining the inner diameter of the wall of the gas pipe 18. Rotation of the crank arm 28 by the scan motor 30 causes the scan roller 20 at either end thereof to similarly rotate resulting in the scan assembly 10 being propelled by the scan rollers 20 through the gas pipe 18.

Figure 3:
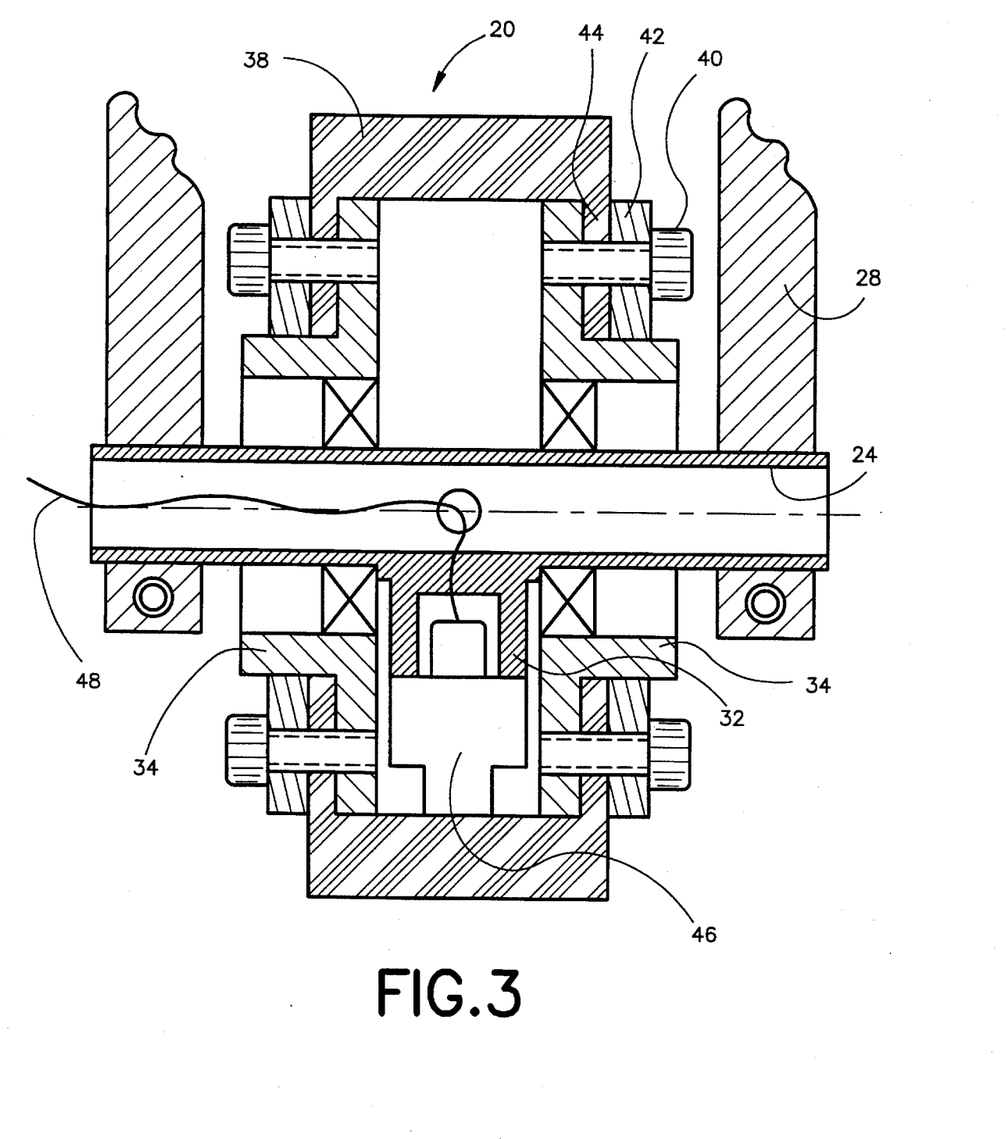
FIG. 3 is a cross-sectional view of the scan roller of the scan assembly of FIG. 1.

Referring now to FIG. 3, a cross-sectional view of a scan roller 20 rotationally mounted to the axle 24 is illustrated. The scan roller 20 includes a hub 32 through which an axle 24 is received and attached thereto, a pair of spaced-apart side plates 34 between which the hub 32 is interposed, a pair of sealed beatings 36 for rotational mounting of the side plates 34 to the axle 24 and the hub 32, and a polymer tire 38. The polymer tire 30 is attached to the side plates 34 by fasteners 40 which are received through both a backing plate 42 and an inwardly directed lip of the tire 38 which threadingly engages the side plate 34. An ultrasonic transducer 46 is received within the scan roller 20 and is attached to the hub 32 therein. An electrical conductor 48 is connected to the ultrasonic transducer 46 and passes through the axle 24 permitting electrical actuation of the transducer 46 resulting in the production of interrogating ultrasonic pulses which are transmitted through the wall of the tire 38 into the wall of the gas pipe 18. The return pulses resulting from any interfaces encountered by the interrogating pulses are likewise received by the transducer 46 through the wall of tire 38. Such interfaces include, but are not limited to, the surface defining the inner diameter of the wall of the gas pipe, the surface defining the outer of the wall of the gas pipe 18, and any imperfections and/or flaws within the walls of the gas pipe 18.

Figure 4:
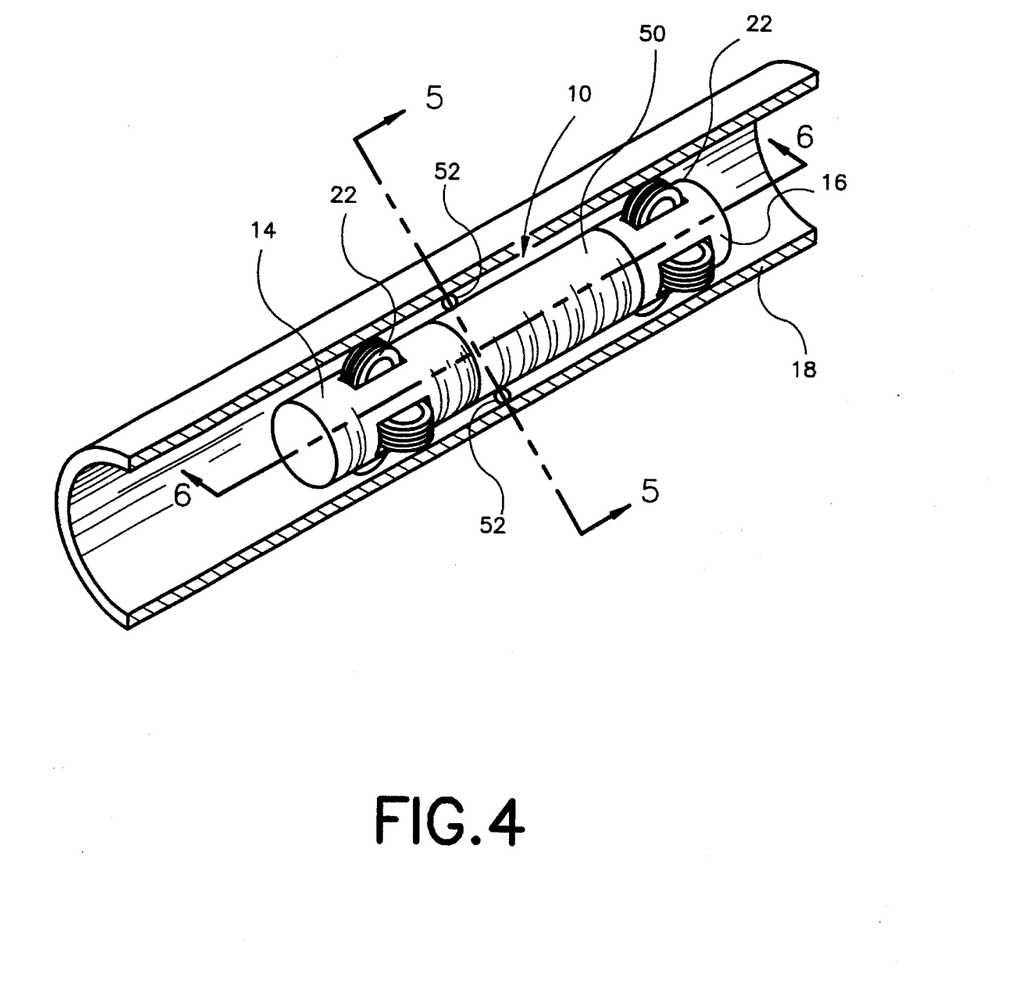
FIG. 4 is a perspective view, partially cut-away in cross-section, of an alternative embodiment of a scan assembly in accordance with the present invention.
Figure 5:
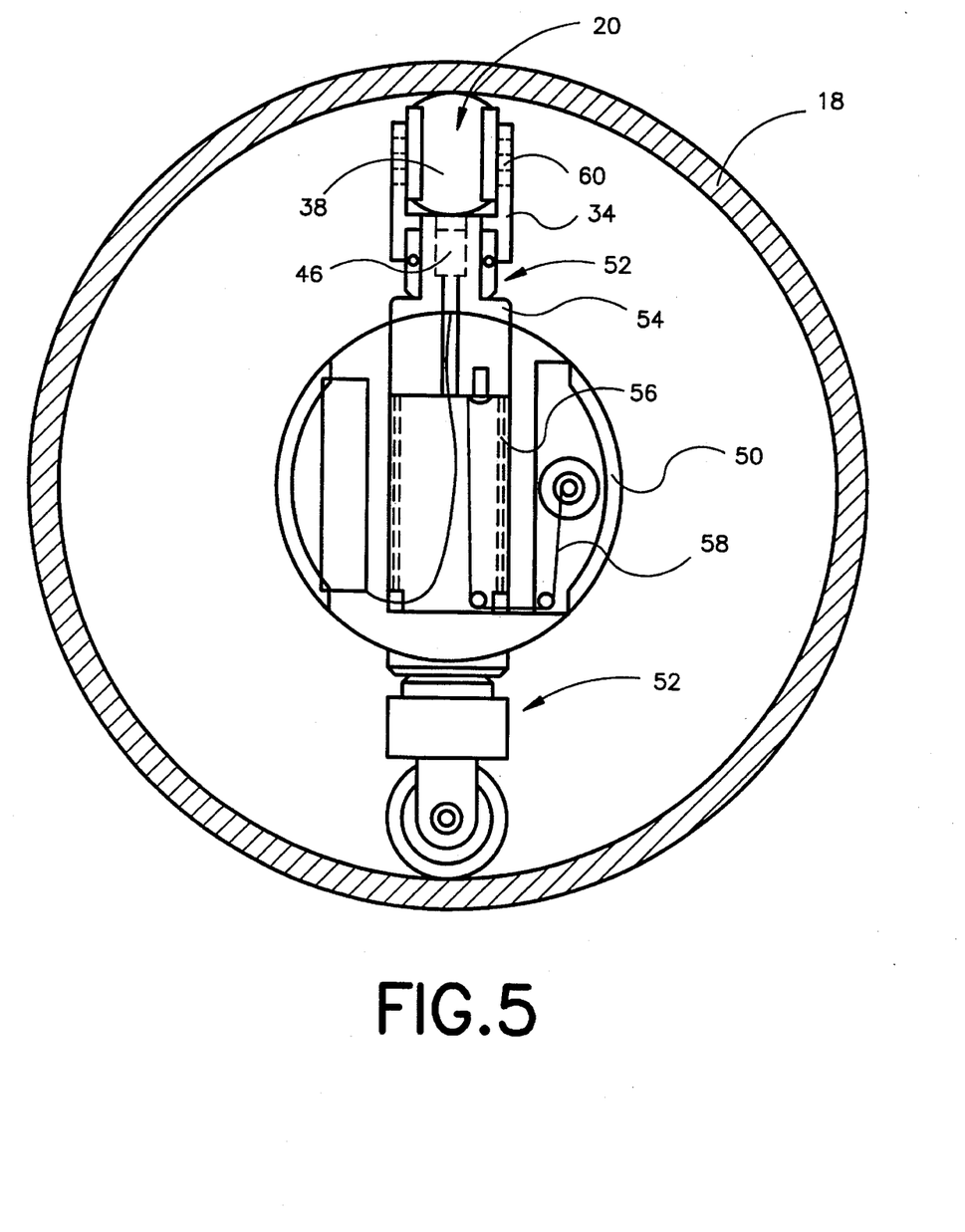
FIG. 5 is a partial cross-sectional view of the scan assembly of FIG. 4 taken substantially along lines 5—5 in FIG. 4.

A perspective view of another type of scan assembly 10 is shown in FIG. 4. In this instance, the scan assembly 10 is not self-propelling but requires the application of an externally applied force thereto to move though the gas pipe 18. In this case, the scan assembly 10 includes a sensor section 50 interposed between the front section 14 and the rear section 16 of the scan assembly 10 and rotatable about the longitudinal axis of the scan assembly 10. Referring now to FIG. 5, each scan roller 20 is part of a scan roller assembly 52, and two scan roller assemblies 52 are received within the sensor section 50 and are angularly positioned 180 degrees relative to one another. Each scan roller assembly 52 is comprised of a telescoping scanning arm 54, a scan roller 20 rotatably connected to one end of the scanning arm 54, an extension spring 56 contacting the other end of the scanning arm 54 and biasing arm 54 radially outwardly from the sensor section 50, and a retraction cable 58 which assists in withdrawing the scanning arm 54 into the sensor section 50. Each retraction cable 58 is connected to a linear variable distance transducer (not shown) which provides information as to the radius of the inner diameter of the gas pipe 18 as a function of the angular orientation of the scan roller assembly 52. Such information can be utilized to provide data as to the shape and ovality of the inner diameter of the gas pipe 18.

When the scan roller assemblies 52 are radially extended relative to the sensor section 50, their associated tires 38 grippingly and pliantly engage the surface defining the inner diameter of the wall of the gas pipe 18. Conversely, when the scan roller assemblies 52 are in the fully retracted condition, their associated tires 38 are within the sensor section 50. In either case, the tires 38 are formed from a low bulk modules polymer material to provide an optimum mechanical impedance for the passage of ultrasonic pulses therethrough. It should be noted that the ultrasonic transducer 46 might be mounted externally of the scan roller 20, as shown by the phantom lines in FIG. 5. When the transducer 46 is so mounted, the scan roller 20 will be provided without an axle 24, and will be supported for rotation by outwardly directed journals 60 attached to the side plates 34.

Figure 6:
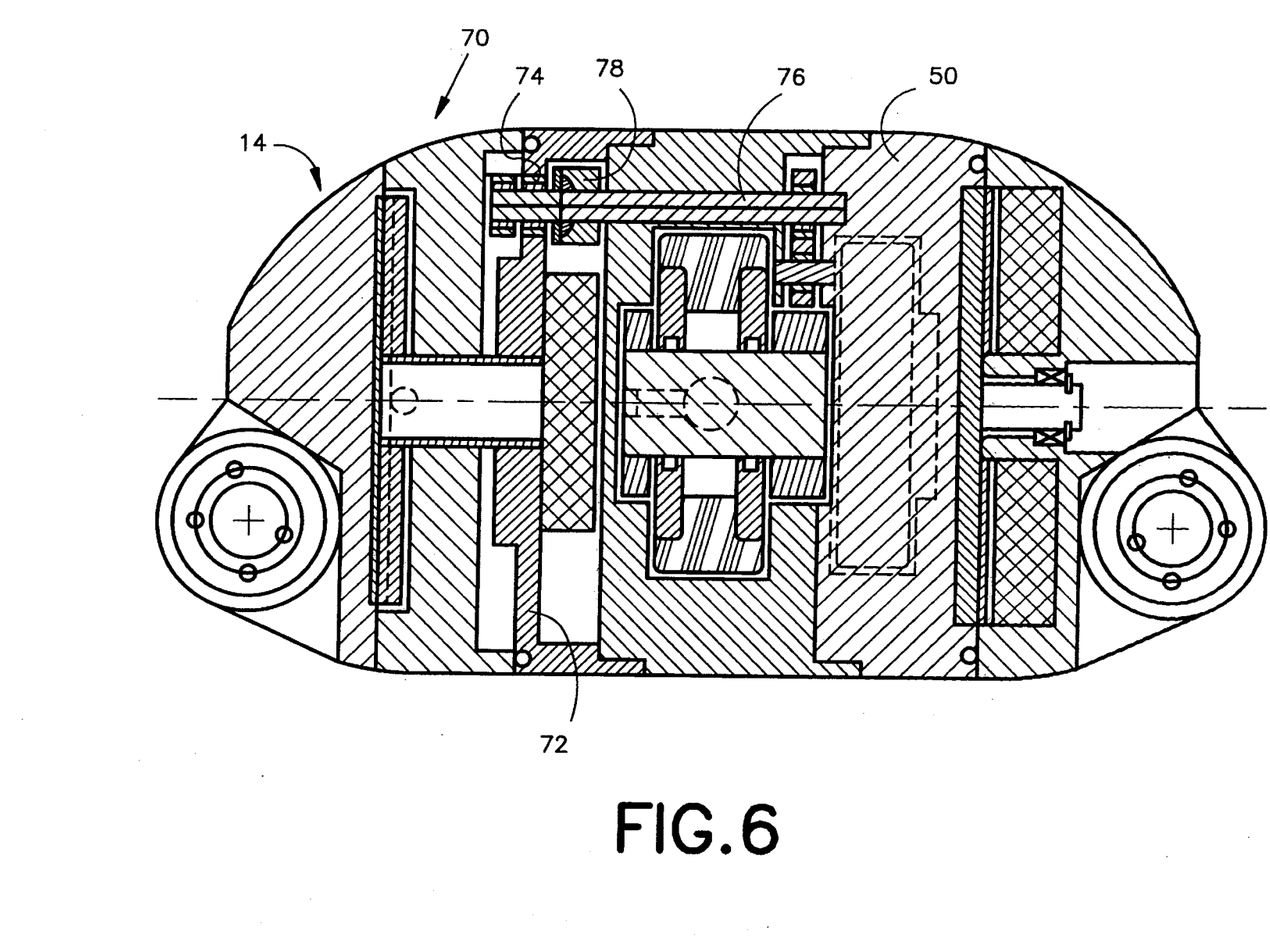
FIG. 6 is a partial cross-sectional view of the scan assembly of FIG. 4 taken substantially along lines 6—6 in FIG. 4, showing the drive for the sensor section within same.

Referring now to FIG. 6, the drive for the sensor section 50 is illustrated. The drive is comprised of a reversible electric motor 70 located in front section 14 of the scan assembly 10. The output shaft of motor 70 is coupled to the sensor section 50 causing rotation thereof. A ring gear 72 is similarly coupled to the output shaft of the motor 70 and engages an idler gear 74 which is connected to a shaft 76 within the sensor section 50 via a ball sprague clutch assembly 78. The shaft 76 is, in turn, connected to two retraction cables 58 (FIG. 5), each of which is connected to a scanning arm 54. During clockwise rotation of the output shaft of motor 70, the ball sprague clutch assembly 78 is disengaged and the sensor section 50 is rotated by a motor 70 and each scanning arm 54 moves radially outwardly under the urging of a spring 56 causing its associated tire 38 to contact the surface defining the inner diameter of the wall of the gas pipe 18. If an obstruction in the gas pipe 18 is encountered, the motor 70 is stopped and reversed causing its output shaft to rotate counter-clockwise. In this situation, the ball sprague clutch assembly 78 becomes engaged and the motor 70 reels in, or retracts, the cables 58 causing the scanning arms 54 to retract radially inwardly into the sensor section 50. It should be noted that the wheels 22 on the front section 14 and the rear section 16 of the scan assembly 10 prevent rotation of these sections with respect to the sensor section 50 as the scan assembly 10 moves through the gas pipe 18.

Figure 7:
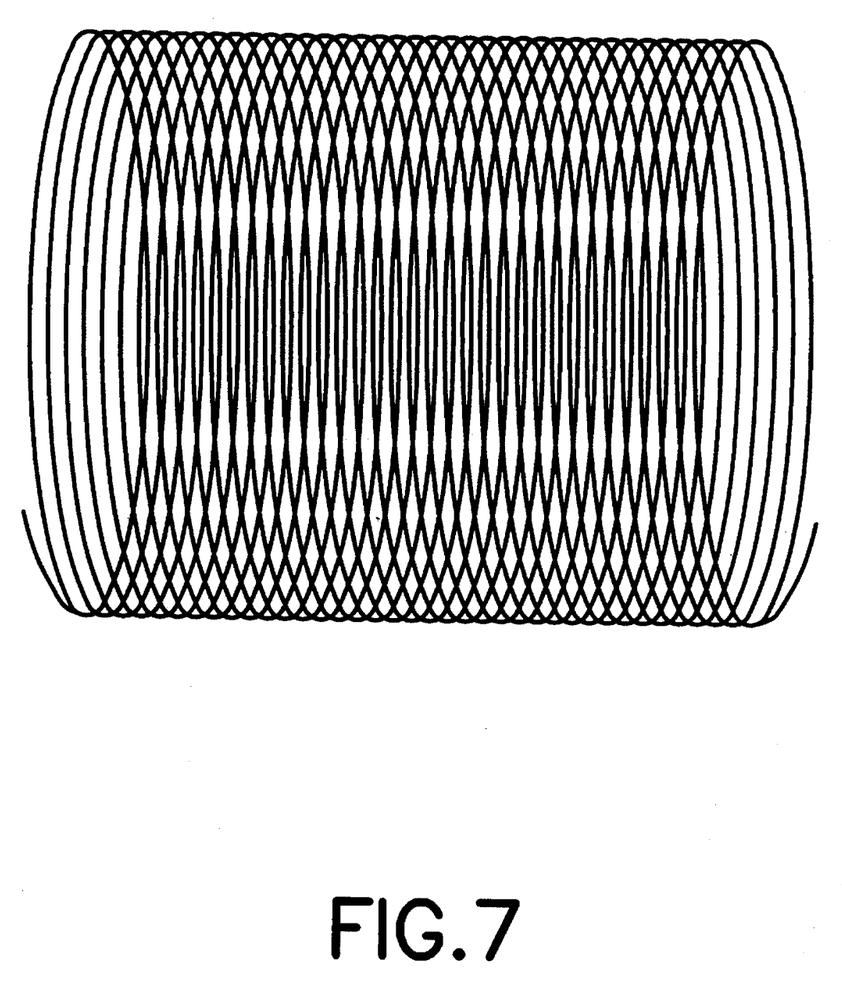
FIG. 7 illustrates a typical helical scan pattern produced by a scan assembly such as the scan assemblies depicted in FIG. 1 and FIG. 4.

As previously stated, each scan roller 20 has an ultrasonic transducer 46 associated therewith. As tire 38 rotates, the ultrasonic transducer 46 associated therewith produces an interrogating pulse which passes through the tire 38 and intercepts the surfaces defining the inner diameter and the outer diameter of the gas pipe 18 and any imperfections or flaws within the wall of the gas pipe 18. The surfaces defining the inner diameter and the outer diameter of the gas pipe 18 and any imperfections or flaws within the wall of the gas pipe 18, in turn, cause the individual return pulses to be transmitted back to the ultrasonic transducer 46. As the scan assembly 10 moves axially within the gas pipe 18, the sensor section 12, 50 rotates such that tires 38 scan the wall of the gas pipe 18, creating a helical scan pattern, as illustrated in FIG. 7. The helical path traveled by a tire 38 about the wall of the gas pipe 18 is referred to as a scan line. If the ultrasonic transducer 46 associated with each scan roller 20 is selectively actuated as the scan assembly 10 moves within the gas pipe 18, a model of the wall of the gas pipe 18 showing the wall thickness and sub-surface imperfections, such as cracks, inclusions, flaws or imperfections, can be generated.

The present invention is directed to improving the effective signal-to-noise ratio of the individual return pulses which can be utilized to generate the foregoing model of the wall of the gas pipe 18. The method of the present invention takes into account the rate of penetration of the ultrasonic interrogating pulse and the angle at which it intercepts the surfaces of the material under test. The pressure wave nature of ultrasonic interrogating pulses causes the directional scattering of pulse energy to be in accordance with the conventional physical laws of reflection and refraction. The direction of the ultrasonic interrogating pulse into the material under test can be controlled by the angle of the ultrasonic transducer with respect to the surface of the material under test. In the preferred embodiment, the incident angle of the interrogating pulse into the pipe wall is perpendicular to a line drawn tangent to the surface defining the inner diameter of the pipe at the point of entry. Once the ultrasonic interrogating pulse enters the material under test, the direction of the pulse will remain substantially constant until a discontinuity is encountered causing a return pulse to be produced. Ideally the return pulse will substantially backtrack the same path of the ultrasonic interrogating pulse, and thus, the return pulse returns to the inside surface of the pipe wall at the point of entry. Because the scan rollers move relatively slow in comparison to the speed of travel of the interrogating and return pulses, the scan roller is still in position to receive the return pulse.

A problem occurs, however, when conventional ultrasonic systems are utilized on materials having uneven surfaces since such surfaces create a multitude of entry angles for the ultrasonic interrogating pulses. Each of these entry angles can cause the ultrasonic interrogating pulse to be deflected or refracted in a direction such that any return pulses will not be intercepted by the ultrasonic transducer. In effect, the return pulses will be distributed randomly to various locations on the surface of the material under test forming a substantially circular pattern around the ultrasonic transducer 46. This same problem occurs when the inside surface of the pipe being inspected is covered by debris or contaminates which interfere with the transmission of ultrasonic energy from the scan rollers 20 into the pipe wall. Further, an imperfection of or a degradation to the pipe wall which comprises many different surfaces having different angles can also cause random scattering of the return pulses such that only a minimum number are received by the ultrasonic transducer. In either of these cases, since virtually no return pulses are received by the ultrasonic transducer, no viable measurement data is generated. This absence of scan data in the measurement data stream is referred to as a "drop-out." If this condition occurs frequently, the inspection process has little or no value.

In order to overcome the problems associated with a random distribution of return pulses, it has been determined that varying or modulating the scan rate greatly increases the probability of receiving the randomly reflected return pulses. If the scan rate is varied or modulated as scan assembly 10 advances down gas pipe 18 so that the section of gas pipe 18 inspected by a single revolution of sensor section 12, 50 is inspected more than once at different scan rates, a much higher percentage of the randomized return pulses positioned either in front of or behind the ultrasonic transducer 46 along the scan line will be located under and received by the ultrasonic transducer 46. Thus, with the multiple passes over a single scan line at differing scan rates (i.e., rotational or angular velocities $V_r$) of the transducer, voids or "dropouts" in the measurement data stream are minimized. If such data is placed in memory and collected, a relatively complete measurement data stream can be compiled. In essence, if the surface and/or thickness of the material under test is such so as to create a random distribution of the return pulses oriented in a substantially circular cluster under the ultrasonic transducer 46, the return pulses that typically fall in front of or behind the ultrasonic transducer 46 along the scan line can be received by the transducer 46 so as to produce a measurement data stream for material inspection purposes.

Figure 8:
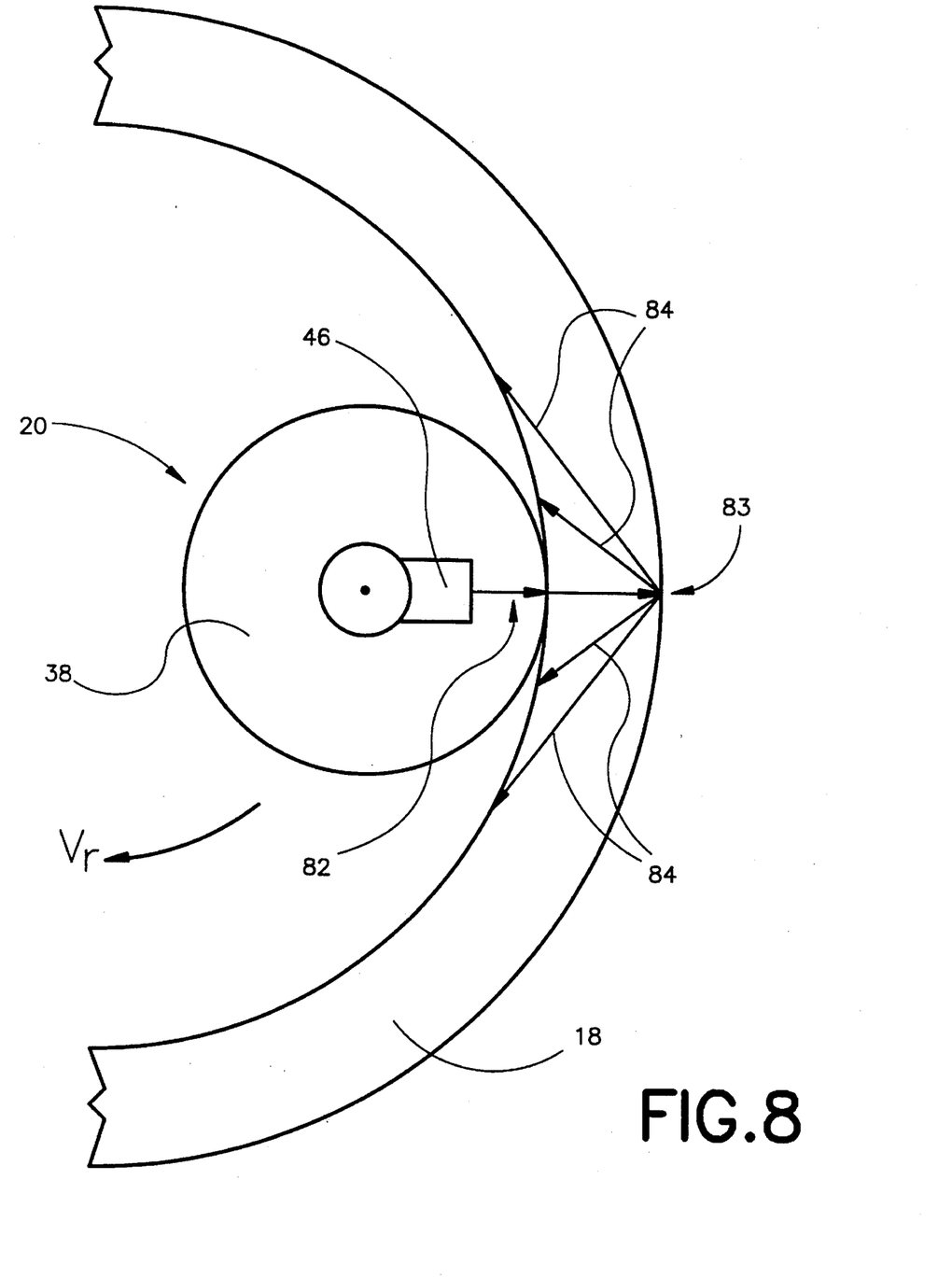
FIG. 8 is a schematic illustration of the scattering of return pulses when an imperfection or flaw is encountered.

This concept is illustrated in FIG. 8 where an interrogating pulse 82 is transmitted by transducer 46, travels through tire 38 of scan roller 20, enters the wall of gas pipe 18 and then encounters an imperfection or flaw 83 in the surface defining the outer diameter of gas pipe 18. The angular velocity or scan rate of scan roller 20 is denoted as $V_r$. The return pulses 84 are scattered in front of, behind, and to the sides (not shown) of scan roller 20. By scanning the section of gas pipe 18 with the imperfection or flaw 83 a second time at faster angular velocity $V_r$, a greater percentage of return pulses scattered ahead of scan roller 20 are received by transducer 46. Conversely, by scanning the same section of gas pipe 18 at a slower angular velocity $V_r$, a greater percentage of return pulses scattered behind scan roller 20 are received by transducer 46. The return pulses which are scattered to either side of the scan line are not receivable without varying the scan line, although the data collected via scan rate modulation can be correlated and the laterally scattered energy accounted for mathematically. Alternatively, a lateral receiver transducer can be included and mounted with the pipe transducer though the complexity of the wiring and space considerations would apparently make such option unattractive.

The degree of modulation in the scan rate between consecutive scans is largely dependant upon the speed of sound in the subject material and the resultant pattern of return pulses in the worse case scattering. It has been determined that up to 1500 percent change in consecutive scan rates is beneficial. The optimum change is largely dependent upon the magnitude of the angular displacement of the return pulses.

The foregoing approach of modifying the scan rate so that the transducer 46 passes over the same section of gas pipe 18 at more than one scan rate in consecutive revolutions of sensor section 12, 50, each number of accurate data points can effectively increase by as much as fifty percent due to the addition data collected from pelleted pulses ahead of or behind transducer 45. Since the exact location of the return pulses on the surface defining the inner diameter of the material under test are unknown, the scan rate can be varied or modulated over a range to capture substantially all of the return pulses positioned ahead of or behind the ultrasonic transducer 46 along a scan line.

Figure 9:
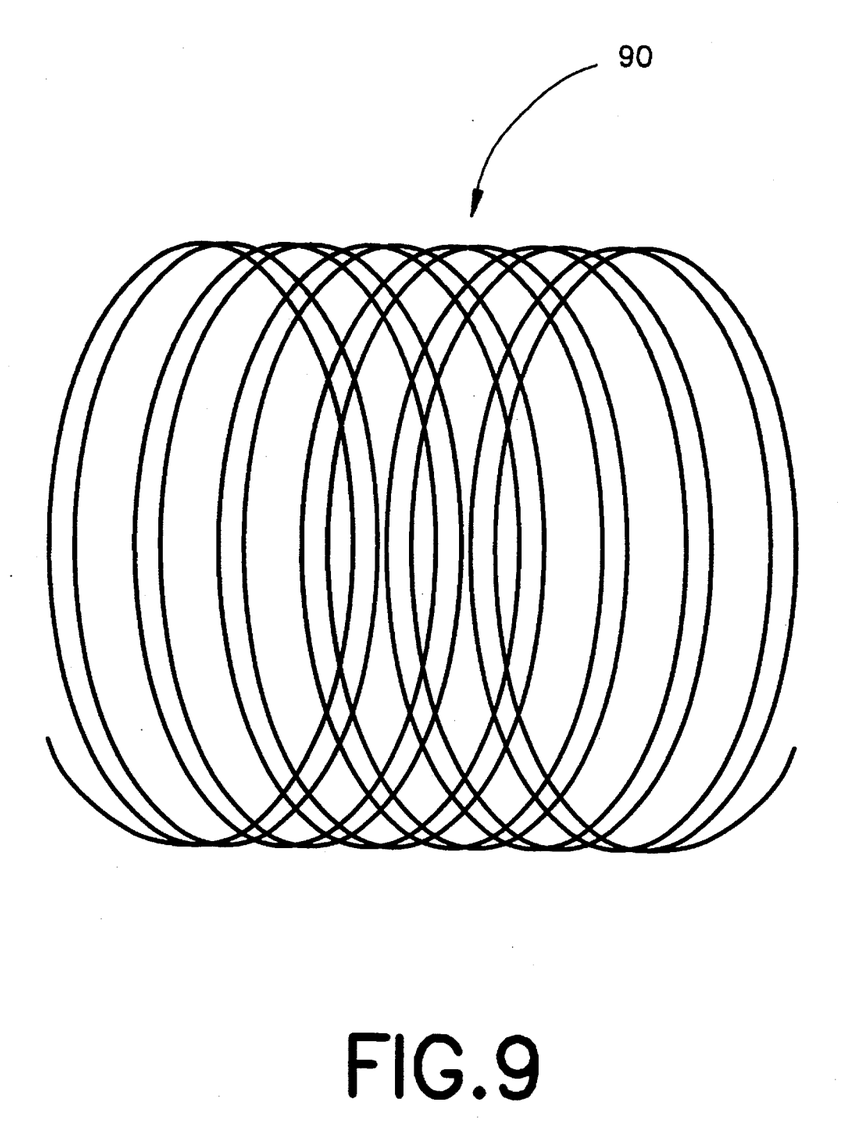
FIG. 9 illustrates a scan pattern produced by a scan assembly such as the scan assemblies depicted in FIG. 1 and FIG. 4, using a scan rate modulation method of the present invention.

In order to implement the present invention, a gravity sensor (not shown) is mounted in either the front section 14 or rear section 16 of scan assembly 10 so that the scan assembly 10 is able to maintain a level orientation as it moves in the gas pipe 18. The motor 70 which rotates sensor section 12, 50, monitors the angular position of sensor section 12, 50 so that the rotation speed thereof can be modulated when sensor section 12, 50 is at the appropriate angular position, that is, at the end of a single revolution. Thus, each revolution of sensor section 12, 50 can be at a different scan rate or rotational velocity $V_r$. As the scan rate is selectively modulated, the axial movement of scan assembly 10 remains constant at a relatively slow speed so that consecutive revolutions of sensor section 12, 50 overlap and scan substantially the same portion of the wall of gas pipe 18. FIG. 9 illustrates a scan pattern 90 produced by modulating the scan rate by switching between two angular velocities $V_{r1}$ and $V_{r2}$, where $V_{r2} > V_{r1}$. The pattern 90 is generated by rotating sensor section 12, 50 a single revolution at $V_{r1}$ followed by a second revolution at $V_{r2}$, thereby substantially overlapping the scan line covered by the scan performed at $V_{r1}$. Thus, more data is collected regarding the portion of gas pipe 18 inspected in the overlap region of the two consecutive scans performed at different scan rates. The same sequence is then repeated in a continuous fashion over the section of gas pipe 18 that is sought to be scanned.

Alternatively, the scan assembly 10 can be configured to "stop and go," or move by increments, as it travels axially down the gas pipe 18 while two or more consecutive scans at different scan rates are taken of the same wall section at each stop of the scan assembly 10. In this embodiment, at each stop, the scan lines completely overlap one another.

Moreover, it will be understood that the invention is not restricted to the particular embodiments described herein, and that many modifications can be made to such embodiments by one skilled in the art without departing from the spirit of the invention or the scope of the claims.

Wherefore, the following is claimed:

1. A method for scanning a surface and cross-section of a wall of an elongated cylindrical object with an ultrasonic scan assembly having a rotatable sensor section capable of rotating as said scan assembly is advanced axially in said cylindrical object, said sensor section including scan means for transmitting and receiving ultrasonic energy, said method comprising the steps of:

advancing said scan assembly in an axial direction along said elongated cylindrical object;

rotating said sensor section of said scan assembly at a first scan rate as said scan assembly advances in said axial direction so as to create a helical scan pattern; and modulating the scan rate of said sensor section as said scan assembly advances in said object whereby a portion of said object scanned at said first scan rate is scanned at a second scan rate.

2. The method of claim 1, wherein said scan rate of consecutive scans vary up to 500 percent.

3. The method of claim 1, wherein said scan assembly is a push rodded system.

4. The method of claim 1, wherein said scan assembly is a robotic system.

5. The method of claim 1, wherein said portion of said object comprises a helical cross-section of said object defined by a single revolution of said sensor section.

6. The method of claim 1, wherein said scan assembly advances in said object at a substantially constant speed.

7. The method of claim 1, wherein said portion of said object scanned at said first scan rate and scanned at said second scan rate completely overlap.

8. The method of claim 1, wherein said portion of said object scanned at said first scan rate and scanned at said several scan rate partially overlap.

9. A scan assembly for scanning a surface and cross-section of a wall of an elongated cylindrical object with the scan assembly having a rotatable sensor section capable of rotating as the scan assembly is advanced axially in the cylindrical object, the sensor section including a scanner for transmitting and receiving ultrasonic energy, the scan assembly comprising:

first means for advancing said scan assembly in an axial direction along said elongated cylindrical object at a first axial rate;

second means for rotating said sensor section of said scan assembly at a first scan rate as said scan assembly advances in said axial direction so as to create a helical scan pattern, said first scan rate based upon said axial rate so that a desired amount of overlap between consecutive rotations of said sensor section occurs; and third means for modulating the scan rate of said sensor section as said scan assembly advances in said object whereby a portion of said object scanned at said first scan rate is scanned at a second scan rate.

\* \* \* \* \*